(12) United States Patent
Probst et al.

(10) Patent No.: US 11,589,785 B2
(45) Date of Patent: Feb. 28, 2023

(54) LEVODOPA SENSOR FOR TIGHT TUNING OF DOSAGE

(71) Applicant: Medtronic, Inc., Minneapolis, MN (US)

(72) Inventors: David Probst, Chandler, AZ (US); Randal Schulhauser, Phoenix, AZ (US); Patrick W. Kinzie, Glendale, AZ (US); Jadin C. Jackson, Roseville, MN (US); Daniel Hahn, Orange, CA (US)

(73) Assignee: Medtronic, Inc., Minneapolis, MN (US)

(*) Notice: Subject to any disclaimer, the term of this patent is extended or adjusted under 35 U.S.C. 154(b) by 67 days.

(21) Appl. No.: 17/176,976

(22) Filed: Feb. 16, 2021

(65) Prior Publication Data

US 2021/0251525 A1 Aug. 19, 2021

Related U.S. Application Data

(60) Provisional application No. 62/976,580, filed on Feb. 14, 2020.

(51) Int. Cl.
| | |
|---|---|
| *A61B 5/1468* | (2006.01) |
| *A61B 5/00* | (2006.01) |
| *A61N 1/05* | (2006.01) |
| *A61K 31/662* | (2006.01) |
| *A61M 5/142* | (2006.01) |
| *A61N 1/36* | (2006.01) |

(52) U.S. Cl.
CPC .......... *A61B 5/1468* (2013.01); *A61B 5/4839* (2013.01); *A61B 5/742* (2013.01); *A61K 31/662* (2013.01); *A61M 5/142* (2013.01); *A61N 1/0534* (2013.01); *A61N 1/36139* (2013.01); *A61M 2005/14208* (2013.01)

(58) Field of Classification Search
CPC ..... A61B 5/1468; A61B 5/4839; A61B 5/742; A61B 5/142; A61B 5/1473; A61B 5/14546; A61K 31/662; A61K 31/198; A61M 5/142; A61M 5/172; A61M 2005/14208; A61N 1/0534; A61N 1/36139; G01N 27/3275; G01N 27/3271
USPC ...... 435/817; 422/82.01; 204/403.14, 403.01
See application file for complete search history.

(56) References Cited

U.S. PATENT DOCUMENTS

| | | |
|---|---|---|
| 2006/0195157 A1 | 8/2006 | Lee et al. |
| 2011/0230735 A1 | 9/2011 | Wolf et al. |

(Continued)

OTHER PUBLICATIONS

Halje et al. "Levodopa-Induced Dyskinesia Is Strongly Associated with Resonant Cortical Oscillations", J. Neurosci. Nov. 21, 2012; 32(47): 16541-16551. doi: 10.1523/JNEUROSCI.3047-12.2012 (Year: 2012).*

(Continued)

*Primary Examiner* — Allen Porter
*Assistant Examiner* — Avery M Foley
(74) *Attorney, Agent, or Firm* — Patterson Thuente IP

(57) ABSTRACT

An enzymatic sensor configured to determine the concentration of levodopa present in a sample according to a current or a resonant frequency produced in response to levodopa interactions with L-amino acid decarboxylase present in the sensor. A processor associated with the sensor determines levodopa concentration and produces dose recommendation or output according to levodopa concentration.

10 Claims, 4 Drawing Sheets

(56) References Cited

U.S. PATENT DOCUMENTS

2017/0226557 A1     8/2017   Wang et al.
2018/0353759 A1*   12/2018   Starr ..................... A61B 5/369

OTHER PUBLICATIONS

International Search Report and Written Opinion, International Application No. PCT/US21/18240, dated Jun. 11, 2021, 11 pgs.

* cited by examiner

LEVODOPA SENSOR FOR TIGHT TUNING OF DOSAGE

CROSS-REFERENCE TO RELATED APPLICATIONS

The present application claims the benefit of U.S. Provisional Application No. 62/976,580 filed Feb. 14, 2020, the disclosure of which is hereby incorporated by reference in its entirety.

FIELD

This disclosure relates to closed loop drug delivery systems and more specifically to a system for controlling the delivery of levodopa or other related drug compounds or formulations based on continuously monitored levels of those drugs or compounds in the body.

BACKGROUND

Dopamine is a neurotransmitter implicated in a number of key functions in the brain, but most notably in regulating movement. Dopamine is produced in the body by decarboxylation of levodopa (L-Dopa) which is itself synthesized from the amino acid L-tyrosine by the enzyme tyrosine hydroxylase. L-Dopa is a precursor to a number of other neurotransmitters, most notably epinephrine and norepinephrine.

Dopamine is unable to cross the blood brain barrier, but L-Dopa is able to cross the barrier and therefore it can be effective to treat diseases of dopamine deficiency such as Parkinson's disease and dopamine-responsive dystonia. L-Dopa enters the central nervous system (CNS) and is then converted to dopamine, raising dopamine levels in the CNS and activating postsynaptic dopaminergic receptors. In this way, administration of L-Dopa can compensate for a decrease in endogenous dopamine.

Several pharmaceutical versions of L-Dopa exist, and it may administered orally or liquid versions may be administered by a duodenal pump. Gastrointestinal uptake of L-Dopa is highly variable and may be inhibited by many dietary options, most significantly fats and proteins. Proteins especially directly compete with the L-Dopa for uptake sites, and can reduce the effective amount of L-Dopa taken up from a given dose. Increasing dosage to account for limited uptake carries its own problems. If a patient's diet on a particular day permits exceptionally high uptake, such dosage excursions can increase associated risks. High L-Dopa peaks in the brain are especially detrimental as they have been associated with disruptive or disabling motor and behavioral complications in Parkinson's patients.

Pharmaceutical L-Dopa that is taken up creates a systemic rise in L-Dopa throughout the body. This results in increased dopamine throughout the entire CNS, not just in therapeutic target areas. L-Dopa administered orally or infused outside of the CNS is converted into dopamine in the peripheral nervous system as well, producing further side effects. Side effects can include hypotension, arrhythmias, nausea, gastrointestinal bleeding, disturbed respiration, hair loss, disorientation and confusion, extreme emotional states (particularly anxiety), vivid dreams or insomnia, auditory or visual hallucinations, effects on learning (evidence indicates it may improve working memory, but simultaneously impairs other complex functions), somnolence and narcolepsy, and a condition similar to stimulant psychosis.

For some patients, deep brain stimulation (DBS) of the basal ganglia can supplement L-Dopa treatment. By implanting leads in either the subthalamic nucleus or the globus pallidus internus, dopaminergic receptors may be directly stimulating, lowering a patient's dopamine needs. DBS is associated with a reduced need for pharmaceutical L-Dopa, but DBS may not fully substitute for L-Dopa treatment.

L-Dopa may be administered with a dopamine decarboxylase inhibitor, e.g., carbidopa, to limit metabolism of L-Dopa in the peripheral nervous system. Dopamine promoters can help limit the effective dose of L-Dopa needed but do not address CNS off-target effects and further require their own dosage tuning in parallel with the dose tuning for L-Dopa.

Thus, clinical management of side effects relies on carefully controlling, or "tight tuning," dosage, but dose control is hindered by the lack of input regarding current body L-Dopa levels outside of observed or experienced effects and side effects. Patient management also presents burdens for providing appropriate dosage, as some patients may not take appropriate quantities of medications (or may split pills to spread out and time doses). Thus, there is a need in the art for a means of controlling L-Dopa dosing based on body L-Dopa levels.

SUMMARY

Embodiments of the present disclosure relate to devices and method for L-Dopa detection, measurement, and dosing. It should be understood that while this disclosure refers to L-Dopa throughout, the closed loop system and other concepts described herein could also be used for other drugs, compounds, or formulations that rely on an enzymatic mechanism for metabolization.

Embodiments of the present disclosure are directed to an enzymatic L-Dopa sensor. L-amino acid decarboxylase may integrated or encapsulated in a sensor layer. Electrons released by the oxidation of L-Dopa by the decarboxylase may be detected by an associated electrode or harmonic circuit. The resulting current or resonance frequency may be interpreted by a processor to determine an L-Dopa concentration of a sample.

Embodiments of the present disclosure may incorporate an L-Dopa sensor with an L-Dopa dosage or delivery system. A processor may be configured to determine an appropriate dosage recommendation that can be displayed on a pump as a recommended pump setting.

The above summary is not intended to describe each illustrated embodiment or every implementation of the subject matter hereof. The figures and the detailed description that follow more particularly exemplify various embodiments.

BRIEF DESCRIPTION OF DRAWINGS

Subject matter hereof may be more completely understood in consideration of the following detailed description of various embodiments in connection with the accompanying figures, in which.

Figure 1:
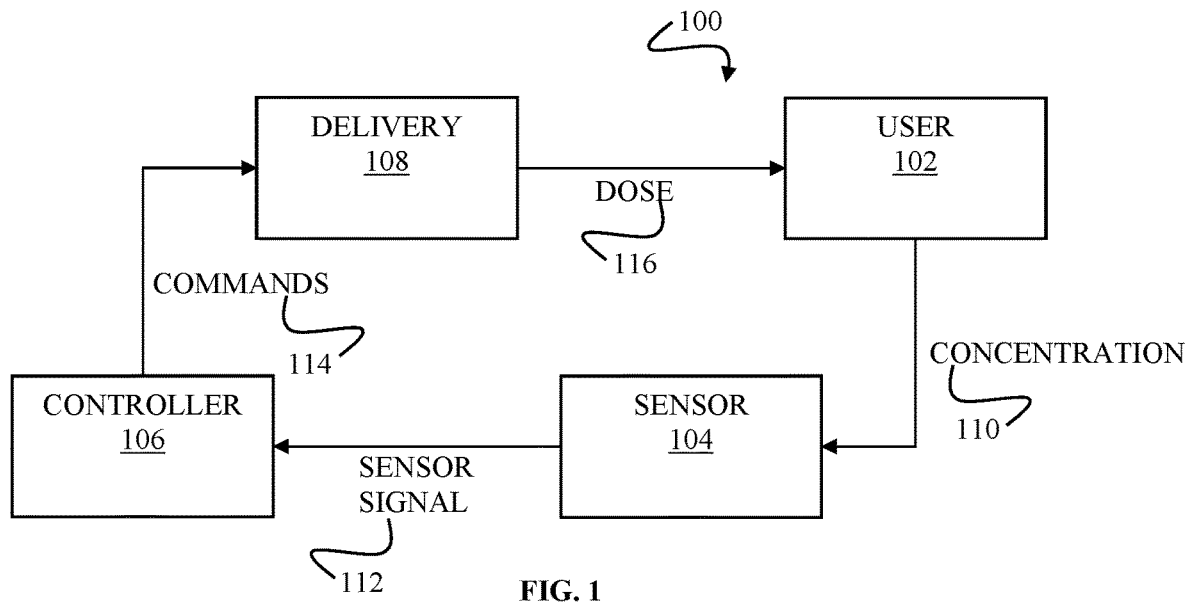
FIG. 1 is a block diagram of a closed loop levodopa system, according to embodiments of the present disclosure.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Embodiments of the present disclosure provide for an open or closed loop analysis system for levodopa (L-Dopa). Embodiments provide for oral dose recommendations and regulation of infusion rate for pharmaceutical L-Dopa based on feedback from a body concentration measurement. Embodiments provide for amperometric or spectroscopic concentration measurements, either in conjunction with a closed loop system or as a standalone measurement system. In embodiments, the system is a control system for regulating the rate of L-Dopa infusion into the body of a user based on an L-Dopa concentration measurement taken from the body of the user. The L-Dopa infusion may be orally, intravenously, or otherwise administered. Embodiments may stimulate L-Dopa production by the body of the user, with stimulation settings variable according to feedback from the L-Dopa detection system.

Referring now to FIG. 1, a block diagram depicts a closed loop system 100 for L-Dopa detection and delivery, according to embodiments of the present disclosure. The closed loop system 100 comprises an L-Dopa sensor 104, a controller 106, an L-Dopa delivery vector 108, and a user 102. The L-Dopa sensor 104 takes a L-Dopa concentration measurement 110 from the body of the user 102. The sensor 104 converts the concentration into an electrical signal 112 which is sent to the controller 106. Controller 106 determines a dose according to the signal 112 and produces commands 114 for the delivery vector 108. Delivery vector 108 responds to the commands 114 by delivering a dose 116 of L-Dopa to the user 102.

Sensor 104 may be an enzymatic sensor, an impedance sensor, or otherwise determine blood concentration of L-Dopa. Controller 106 may generally comprise processor, memory, and software necessary to analyze signal 112 and produce commands 114. Delivery vector 108 may generally comprise oral pharmaceutical L-Dopa or an infusion system for liquid pharmaceutical L-Dopa. Controller 106 may be configured to produce commands 114 that produce a proper dose 116 according to the particular delivery vector 108.

In embodiments, sensor 104 and controller 106 may share a housing, which may be implantable or external to the user 102.

In embodiments, controller 106 and delivery vector 108 may share a housing, which may be implantable or external to the user 102. For example, delivery vector 108 may be an infusion pump in a shared housing with controller 106, or delivery vector 108 may be a screen on the housing of controller 106 that presents oral dose 116 data to the user 102. In embodiments, controller 106 may have its own housing and delivery vector 108 may have its own housing, e.g., a separate infusion pump, or may be in a form which does not require housing at all, e.g., a phone app which presents dose data to the user. When controller 106 and delivery vector 108 are not physically proximate to one another, they may communicate over a greater distance, e.g., via wireless signals.

Sensor 104 may comprise a point of care (POC) sensor, an acute sensor, or a chronic sensor, depending on the needs or desires of a particular user 102. Embodiments of sensor 104 may be configured to differentiate between pharmaceutical and endogenous L-Dopa.

A POC sensor may be favored by a user seeking discrete measurements of L-Dopa throughout use, and could provide feedback regardless of the delivery vector employed. For example, a user with an implanted deep brain stimulation (DBS) therapy system may use a POC sensor to obtain inputs for initial DBS stimulation setup or to update DBS stimulation settings, leading to better outcomes and improved therapy management. A POC sensor may generally be manually operated or triggered by a user on themselves, or by a health care professional. POC sensors may be applicable for immediate feedback, e.g., to determine an L-Dopa blood concentration associated with a particular symptom which is currently being experienced.

Acute continuous measurement of L-Dopa may provide real-time feedback on the user's body concentration and response to an L-Dopa dose and may be particularly informative in automated delivery scenarios. Acute monitoring may generally be for a fixed period, e.g., 3-7 days. Acute monitoring may be applied to determine a user's response to a new dose of orally administered pharmaceutical L-Dopa or a new DBS setting. Acute monitoring may supplement information provided to a physician as part of a tool or system for longitudinal or remote monitoring, such as in a therapy application, digital health platform, or telehealth system Chronic measurement of L-Dopa may be utilized for a true closed loop system, monitoring a user's disease state over long periods of time and adjusting L-Dopa or stimulation dosage according to detected L-Dopa levels and body responses to dosage/infusion/stimulation. Chronic measurement may be tied to an automatic feedback system, which may automatically adjust pharmaceutical L-Dopa dosage or DBS settings according to readings. Chronic measurement may be tied to a manual system, and simply provide long-term data on a user's response to changes in dosage, progression of disease and treatment, etc. Embodiments may incorporate a sensor implanted in the brain, permitting direct measurement of on-target L-Dopa dosage. Chronic monitoring may supplement information provided to a physician as part of a tool or system for longitudinal or remote monitoring, such as in a therapy application, digital health platform, or telehealth system.

Figure 2A:
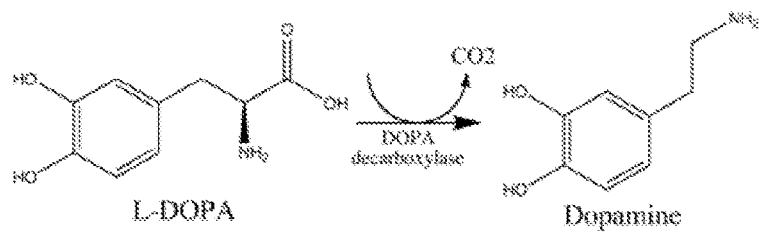
FIGS. 2A-2D depict the reaction between L-Dopa and DOPA decarboxylase.

L-Dopa is converted to dopamine through interaction with the enzyme aromatic L-amino acid decarboxylase (DOPA decarboxylase), as depicted in FIG. 2A. By incorporating DOPA decarboxylase in an enzymatic sensor, L-Dopa present in a sample applied may be detected through interaction with the DOPA decarboxylase.

Figure 2B:
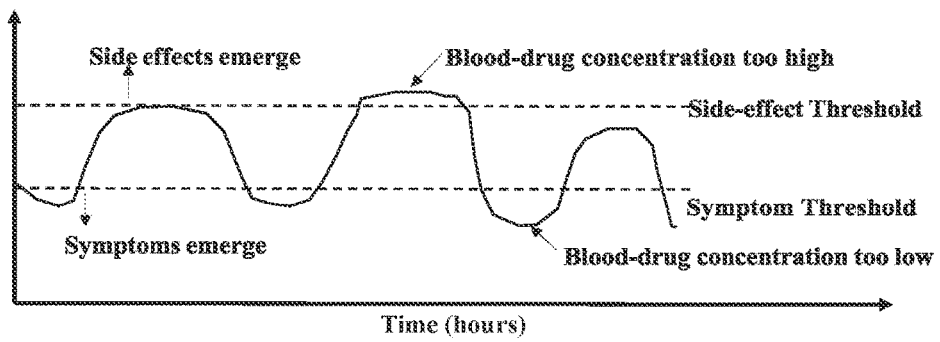
Figure 2C:
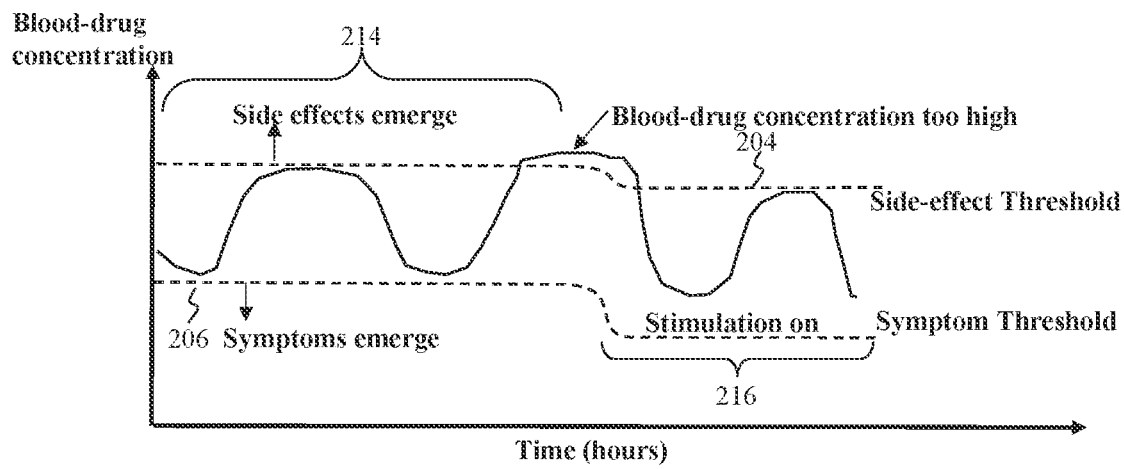
Figure 2D:
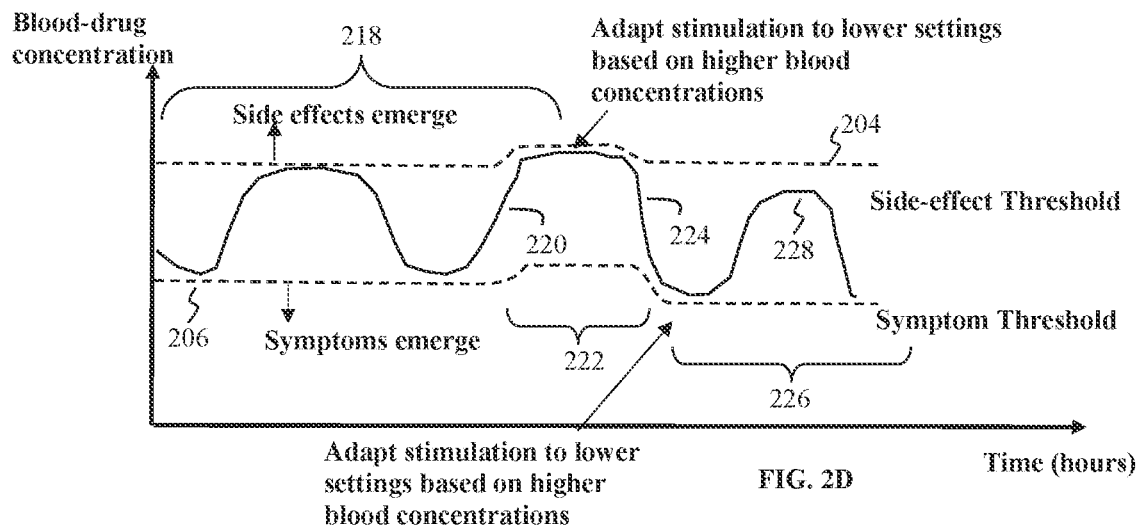

Referring now to FIG. 2B-FIG. 2D, a series of graphs depicting an example tight-tuning process is shown, according to embodiments of the present disclosure. Each of FIG. 2B-FIG. 2D depict time along the x-axis and blood-drug concentration (of levodopa) along the y-axis.

FIG. 2B demonstrates the problem with non-responsive dosing. Conceptually, the target dosage 202 is shown in green, with an upper boundary 204 representing the threshold at which a patient begins to experience side-effects, and a lower boundary 206, below which symptoms begin to emerge. A patient's goal is to maintain their drug administration such that they are above the symptom threshold, yet below the threshold above which side-effects are seen. When a patient's dosage is too high and their cerebrospinal fluid-drug or blood-drug concentration rises above upper boundary 204, at at point 210, the severity of the side effects they experience may be significant enough to offset the relief of their symptoms and/or interfere with their daily life. When a patient's dosage is too low and their blood-drug concentration drops below lower boundary 206, at point 212, they may not receive adequate relief from their symptoms and experience an associated disruption of their quality of life. Line 208 demonstrates patient response as measured using a point-of-care sensor, an acute sensor, or a continuous sensor, each as described in the present disclosure.

When the dosage remains static, excursions like those seen at points 210 and 212 may be unavoidable. An excursion above upper limit 204, such as point 210, may occur following any dose delivery, particularly if dosage is periodic rather than continuous (if pharmaceutical L-Dopa is taken orally, for example). High excursions such as point 210 may also occur if a dose is taken off schedule or if a patient's routine changes, such that metabolism of the dose is slower than presumed when the dose was calculated. High excursions such as point 210 may be associated with motor or cognitive side-effects, such as dyskinesias, psychosis, changes in mood or mental state, or aggressive behavior, as well as a wide range of common systemic side effects including abnormal heart rhythm, difficult or painful urination, excessive nausea or vomiting, or hypotension. High excursions such as point 210 may also exacerbate uncommon and rare side effects including blurred or double vision, hot flashes, spasms of the eyelid, loss of bladder control, chills, fever, loss of appetite, and pain or swelling of the face or lower extremities.

An excursion below lower limit 206, such as point 212, may occur near the end of a dose period in the lead-up to the next dose period, during which a previous dose may be depleted before the next dose is taken by the patient or otherwise delivered to the patient. Low excursions such as point 212 may result from a disruption in the dose delivery schedule, or changes in the patient's routine that result in increased metabolism or elimination of the drug. Low excursions such as point 212 may be associated with an increase or resurgence in symptoms. For patients with Parkinson's, symptoms may include tremors or other muscular symptoms such as stiffness or rigidity, difficulty with mobility or coordination, involuntary or slowed movement, or rhythmic contractions. Other Parkinson's symptoms include sleep disturbances, restless sleep, difficulty speaking, urinary incontinence, reduced facial expressions, constipation, difficulty with memory, or loss or distortion of sense of smell.

The overall pattern of line 208, where the patient's blood-drug concentration fluctuates between high excursions such as point 210 and low excursions such as point 212, is difficult to prevent in a fixed dose model due to factors which can be difficult to regulate, such as the patient's activity level and diet. The patient, as a result, is continually pulled back and forth between the disability of their symptoms and the danger of the side effects.

The graph in FIG. 2C demonstrates the effect of an electrical stimulation system, such as deep brain stimulation (DBS) on the tuning of a patient's blood-drug concentration level. First area 214 closely resembles the target dosage area 202 of FIG. 2B. When stimulation is then added, in second area 216, the lower limit 206 drops, making a lower dose of pharmaceutical L-Dopa effective for the patient to alleviate symptoms. Having a lower effective dose has an overall positive effect on the patient's treatment and can lengthen the timeline for concerns related to the long-term effects of L-Dopa therapy.

However, it is notable that upper boundary 204 is also lowered by the effect of electrical stimulation. Therefore, although the addition of electrical stimulation therapy can provide improvement for patients on L-Dopa therapy, it does not effectively alleviate concerns related to high blood-drug concentration side-effects.

The graph in FIG. 2D demonstrates the effect of the disclosed closed-loop L-Dopa treatment system. The graph in FIG. 2D may also serve to demonstrate patient or provider responses to blood-drug concentration readings taken with the disclosed point-of-care or acute L-Dopa sensors. The examples in FIG. 2D are discussed generally assuming a treatment program incorporating both electrical stimulation and pharmaceutical L-Dopa, but the principles likewise apply to a treatment program using only L-Dopa. L-Dopa delivery may be by oral capsules, liquids, or aerosols, or by internal or external infusion pump delivery, or any other method. Pump delivery may be by an implanted pump, an externally carried pump, or any other infusion pump design. Pump delivery may generally be to the duodenum, but other delivery sites, such as the intrathecal or subarachnoid space of the spine, are also envisioned. In embodiments using both electrical stimulation and L-Dopa for treatment, both devices may be implanted in a single housing or a single uniform device may deliver both forms of treatment.

In first area 218 an initial L-Dopa dose and electrical stimulation setting are established.

At point 220, monitoring of the patient's blood-drug concentration indicates that the patient's blood L-Dopa concentration is rising and an algorithm determines the concentration may exceed the upper limit 204 and cause the patient to experience side effects. In response, the closed loop system may automatically reduce the electrical stimulation setting to reduce the effect of the electrical stimulation, shifting the brain's tuning parameters to the drug concentration, and thereby increase upper limit 204 (see second area 222) or may recommend to a patient or provider to reduce the electrical stimulation setting. In embodiments, the system may alternatively or in addition reduce or recommend reducing a continuous or upcoming dose of L-Dopa. In embodiments, the reduction in stimulation settings or L-Dopa dose may be recommended by a provider according to a reading at point 220 taken using acute or point-of-care blood-L-Dopa concentration measurement. In embodiments, a patient may monitor their own blood-drug concentration using an acute or point-of-care measurement and make the necessary adjustments to their stimulation settings or dosage according to training or instruction received from a provider.

Likewise, at point 224, the system detects a decrease in blood-drug concentration and determines that lower boundary 206 may be crossed, resulting in the patient experiencing symptoms. In response, the system adapts in response to the lower blood-drug concentration to prevent a low excursion, as at area 226. In embodiments, the system may adapt by increasing electrical stimulation settings to decrease lower boundary 206. The system may adapt by decreasing the infusion rate of a drug pump delivering L-Dopa to the patient, or by recommending a lower subsequent dosage to a patient or provider.

The system is further configured to identify when blood-drug concentration is responding within tuning parameters, as at point 228, and therefore determining that current settings should be maintained.

Amperometric Sensor

Figure 3:
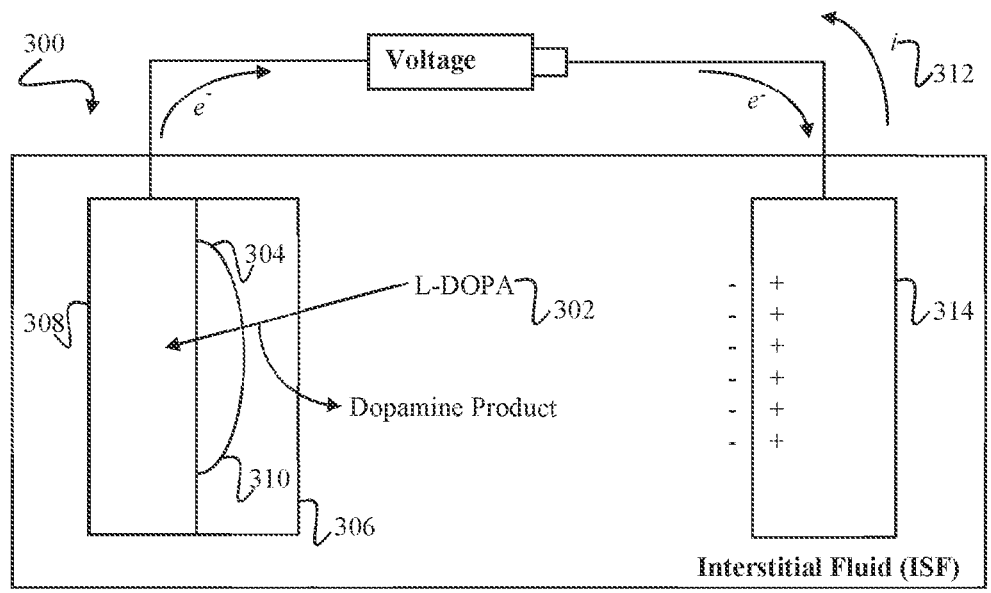
FIG. 3 is an example of an amperometric device for enzymatic detection.

Referring now to FIG. 3, an example of an amperometric device 300 for enzymatic detection is depicted. L-Dopa 302 interacts with L-amino decaroxylase 304 present in an electrochemical layer 306 associated with a working electrode 308. Electrons 310 released by the oxidation reaction are captured by the working electrode 308 and move through the working electrode 308 by potential to produce a current 312. The potential is created by the activity of a reference and a counter electrode 314, which may be shorted together in embodiments, such as example device 300. The current produced is proportional to the level of L-Dopa present in the sample.

Electrochemical Impedance Spectroscopy (EIS)

Figure 4A:
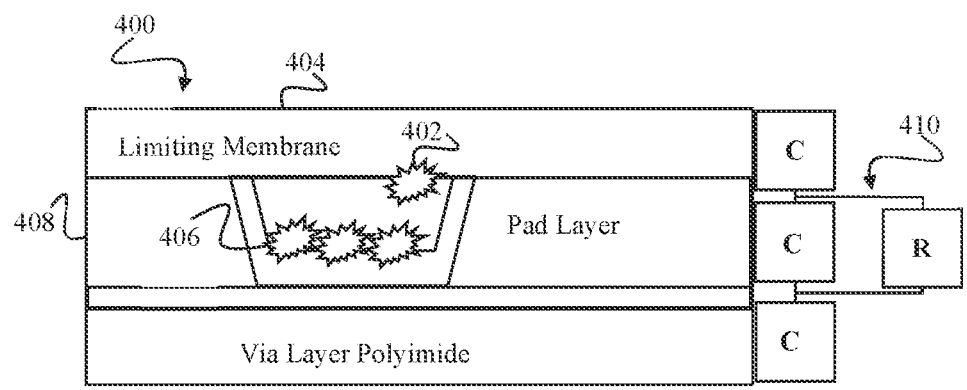
FIGS. 4A-4B show an example of an electrochemical impedance spectroscopy device for enzymatic detection.
Figure 4B:
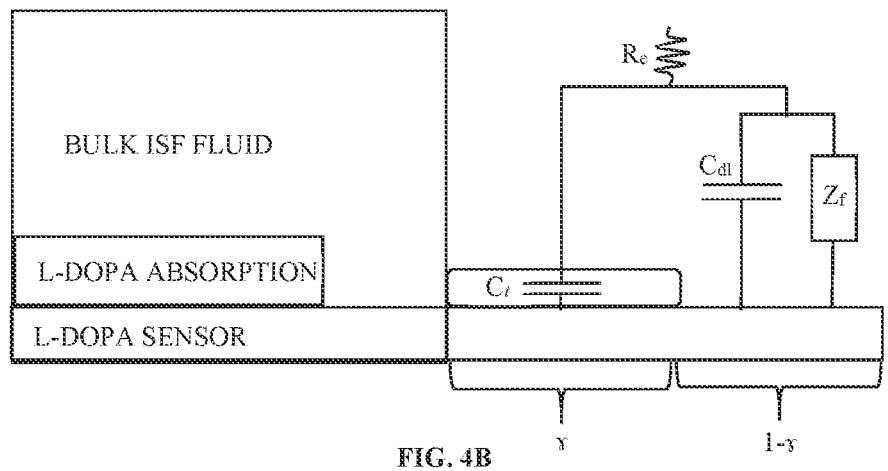

Referring now to FIG. 4A, an example of an EIS enzymatic sensor 400 is shown. L-Dopa molecules 402 in a sample pass through the limiting membrane 404 and interact with DOPA decarboxylase 406 encapsulated in a polyimide pad layer 408. The release of electrons from the oxidation of L-Dopa produces a characteristic response from an attached harmonic oscillating (LRC) circuit 410. In embodiments, LRC circuit 410 may be a Randles or a modified Randles circuit.

Each enzyme interaction in the polyimide layer will exhibit a unique LRC characteristic. The characteristic can in turn be translated to a resonant frequency which can be detected and used to measure the concentration of L-Dopa using electrochemical impedance spectroscopy (EIS). The result is an "ideal" system with reliable results:

$$Z_F = R_t + R_D \frac{\tanh\sqrt{j\omega\delta^2/D_i}}{\sqrt{j\omega\delta^2/D_i}}$$

where $Z_F$=impedance, $R_t$=total resistance, $R_D$=detected resistance, $j=\sqrt{(-1)}$, $\omega$=radial frequency, $\delta$=thickness in which the diffusion should occur, and $D_i$=dissipation factor.

Thus using the enzyme as the molecular recognition element and EIS as the platform, the formation of dopamine can be measured as a rate over time. The enzymatic rates, read as impedance of the circuit, will vary along with the L-Dopa concentration present in a sample over time. These rates can be described through Faradaic interactions by combining Fick's equation of flux and the Nernst equation for current:

$$I = nFAD\left(\frac{[L-DOPA]}{L}\right)$$

where I is the current; n is the number of moles of electrons transferred in the half reaction (number); F is the Faraday constant (C/mol); A is the electrode area (cm$^2$); D is the diffusion coefficient; DOPA is L-Dopa concentration; and L is the distance length in which the reaction can occur (generally the thickness of the diffusion membrane as applied in the present disclosure).

Non-faradaic interactions can be described by using effective capacitance, inductance, Fermi layer, and other electrical properties of the interface.

Figure 5:
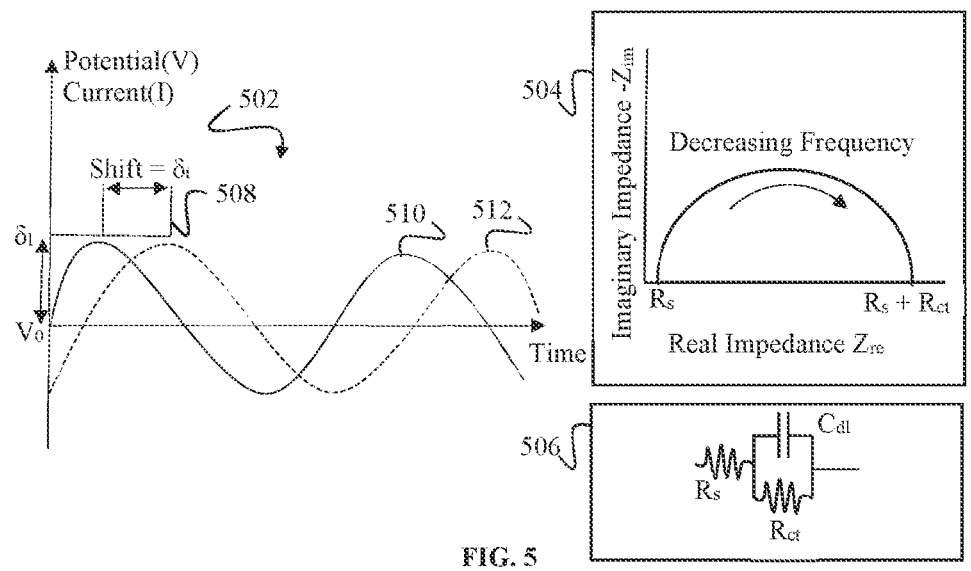
FIG. 5 is an example output of an electrochemical impedance spectroscopy device for enzymatic detection.

In embodiments, use of EIS for the platform provides a non-destructive, ultra-sensitive, rapid, label-free method for measuring L-Dopa concentration. EIS applies an AC voltage, at a unique potential, and measure output impedance. Referring now to FIG. 5, an example output 502 and 504 are depicted for example circuit 506. Example circuit 506 is a standard Randles circuit, with an active electrolyte resistance (Rs) in series with the parallel combination of the double-layer capacitance ($C_{dl}$) and an impedance of a faradaic reaction ($R_{et}$). In embodiments, Cal is modeled using a constant phase element. Output 504, a Nyquist plot, may be realized using the following equation:

$$Z \text{ Total} = Z'(\text{real}) + Z''(\text{imaginary}) = R_s + \frac{R_{et}}{\left(1+(\omega C_{dl}R_{et})^2\right)} + \frac{\omega C_{dl}R_{et}^2}{\left(1+(\omega C_{dl}R_{et})^2\right)}$$

where Z is impedance; R is a resistor in the circuit; C is a capacitor in the circuit; and co is radial frequency.

By detecting differences between the input signal and the output signal, properties the system can be measured based on the change in phase 508 between the input potential 510 and the output current 512. Different properties can be measured based on different LRC circuit designs, each design producing a distinct change in the output signal relative to the properties of the sample.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A levodopa sensor device comprising:
a processor;
a polyimide pad layer with encapsulated L-amino acid decarboxylase;
a harmonic oscillating circuit associated with the polyimide pad layer such that an electrochemical signal produced by interactions of a sample with the encapsulated L-amino acid decarboxylase will produce a resonant frequency on the circuit; and
a computer-readable program code having instructions, which when executed cause the processor to:
detect the resonant frequency obtained from the circuit; and
compute a levodopa concentration based upon the resonant frequency obtained from the circuit.

2. The device of claim 1, further comprising a levodopa delivery component.

3. The device of claim 2, wherein the levodopa delivery component provides a displayed oral dose recommendation according to the calculated levodopa concentration.

4. The device of claim 2, wherein the levodopa delivery component is a duodenal pump.

5. The device of claim 4, wherein the levodopa delivery component provides a displayed pump setting recommendation according to the calculated levodopa concentration.

6. The device of claim 4, wherein the levodopa delivery component provides an automatic adjustment of duodenal pump settings settings according to the calculated levodopa concentration.

7. The device of claim 2, further comprising an electrical stimulation delivery component.

8. The device of claim 7, wherein the electrical stimulation delivery component is a deep brain stimulation (DBS) system.

9. The device of claim 7, wherein the electrical stimulation delivery component provides a displayed electrical stimulation system setting recommendation according to the calculated levodopa concentration.

10. The device of claim 7, wherein the electrical stimulation delivery component provides an automatic adjustment of electrical stimulation system settings according to the calculated levodopa concentration.

* * * * *